United States Patent [19]

Edwards et al.

[11] Patent Number: 6,004,557
[45] Date of Patent: Dec. 21, 1999

[54] VARIANTS OF HUMAN PAPILLOMAVIRUS ANTIGENS

[75] Inventors: Stirling John Edwards, Caburg; John Cooper Cox, Bullengarook; Elizabeth Ann Webb, Eltham; Ian Frazer, St. Lucia., all of Australia

[73] Assignees: CSL Limited, Parkville; The University of Queensland, St. Lucia, both of Australia

[21] Appl. No.: 08/860,165

[22] PCT Filed: Dec. 20, 1995

[86] PCT No.: PCT/AU95/00868

§ 371 Date: Sep. 22, 1997

§ 102(e) Date: Sep. 22, 1997

[87] PCT Pub. No.: WO96/19496

PCT Pub. Date: Jun. 27, 1997

[30] Foreign Application Priority Data

Dec. 20, 1994 [AU] Australia .............................. PN0157/94

[51] Int. Cl.⁶ .......................... A61K 39/00; A61K 39/12; C12N 7/00
[52] U.S. Cl. .................................... 424/192.1; 424/199.1; 424/204.1; 424/186.1; 435/320.1; 435/69.1; 435/235.1; 435/69.7; 536/23.72; 536/23.1; 536/24.3

[58] Field of Search .............................. 424/199.1, 204.1, 424/192.1, 186.1; 435/320.1, 69.1, 172.1, 172.3, 69.7, 235.1; 536/23.72, 23.1, 24.3

[56] References Cited

U.S. PATENT DOCUMENTS 5,719,054  2/1998  Boursnell et al. .................... 435/320.1

FOREIGN PATENT DOCUMENTS

76212/91   11/1991  Australia .
92/05248    4/1992  WIPO .
92/10513    6/1992  WIPO .
QO 9216636 10/1992  WIPO .

OTHER PUBLICATIONS

Stoeppler et al., "Transforming Proteins of the Papillomaviruses", *Intervirology*, vol. 37:168–179, (1994).

*Primary Examiner*—Mary E. Mosher
*Assistant Examiner*—Ali R. Salimi
*Attorney, Agent, or Firm*—Foley & Lardner

[57] ABSTRACT

Variants of human papilloma virus (HPV) E6 and E7 able to elicit a humoral or cellular immune response against HPV in a host animal but not being cell-transforming in the host animal are disclosed, and are useful in treatment or prevention of diseases or conditions involving HPV.

23 Claims, 5 Drawing Sheets

SEQUENCE LISTING

<160> NUMBER OF SEQ ID NOS: 15

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 1
cgctcgagag atctcatatg caccaaaaga gaactgc                37

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 2
cgcccgggca gctgggtttc tctacgtg                          28

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 3
cgcccgggat gcatggagat acacctacat tgcatg                 36

<210> SEQ ID NO 4
<211> LENGTH: 35
<212> TYPE: DNA
<213> ORGANISM: Artificial Sequence
<220> FEATURE:

<223> OTHER INFORMATION: Description of Artificial Sequence: Primer

<400> SEQUENCE: 4
cggtcgacgg atcctggttt ctgagaacag atggg                    35

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 5
gcgcgaattc tattaaggag cccgggatgg ggaatccata tgctgtat     48

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
cgcgagatct ccgaagcgta gagtcacact tg                       32

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 7
cgcccgggta atgttgttcc atacaaacta                          30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
cgcccgggga ggaggaggat gaaatagatg                          30

<210> SEQ ID NO 9
<211> LENGTH: 801
<212> TYPE: DNA
<213> ORGANISM: Artificial Sequence
<220> FEATURE:
<221> NAME/KEY: CDS
<222> LOCATION: (1)..(798)
<220> FEATURE:
<223> OTHER INFORMATION: Description of Artificial Sequence: Gene Fusion

<400> SEQUENCE: 9

```
atg cac caa aag aga act gca atg ttt cag gac cca cag gag cga ccc     48
Met His Gln Lys Arg Thr Ala Met Phe Gln Asp Pro Gln Glu Arg Pro
 1               5                  10                  15 aga aag tta cca cag tta tgc aca gag ctg caa aca act ata cat gat     96
Arg Lys Leu Pro Gln Leu Cys Thr Glu Leu Gln Thr Thr Ile His Asp
             20                  25                  30 ata ata tta gaa tgt gtg tac tgc aag caa cag tta ctg cga cgt gag    144
Ile Ile Leu Glu Cys Val Tyr Cys Lys Gln Gln Leu Leu Arg Arg Glu
         35                  40                  45 gta tat gac ttt gct ttt cgg gat tta tgc ata gta tat aga gat ggg    192
```

```
                Val Tyr Asp Phe Ala Phe Arg Asp Leu Cys Ile Val Tyr Arg Asp Gly
                    50                  55                  60 aat cca tat gct gta tgt gat aaa tgt tta aag ttt tat tct aaa att         240
Asn Pro Tyr Ala Val Cys Asp Lys Cys Leu Lys Phe Tyr Ser Lys Ile
 65                  70                  75                  80 agt gag tat aga cat tat tgt tat agt ttg tat gga aca aca tta gaa         288
Ser Glu Tyr Arg His Tyr Cys Tyr Ser Leu Tyr Gly Thr Thr Leu Glu
                     85                  90                  95 cag caa tac aac aaa ccg ttg tgt gat ttg tta att agg tgt att aac         336
Gln Gln Tyr Asn Lys Pro Leu Cys Asp Leu Leu Ile Arg Cys Ile Asn
                100                 105                 110 tgt caa aag cca ctg tgt cct gaa gaa aag caa aga cat ctg gac aaa         384
Cys Gln Lys Pro Leu Cys Pro Glu Glu Lys Gln Arg His Leu Asp Lys
            115                 120                 125 aag caa aga ttc cat aat ata agg ggt cgg tgg acc ggt cga tgt atg         432
Lys Gln Arg Phe His Asn Ile Arg Gly Arg Trp Thr Gly Arg Cys Met
        130                 135                 140 tct tgt tgc aga tca tca aga aca cgt aga gaa acc cag ctg ccc ggg         480
Ser Cys Cys Arg Ser Ser Arg Thr Arg Arg Glu Thr Gln Leu Pro Gly
145                 150                 155                 160 atg cat gga gat aca cct aca ttg cat gaa tat atg tta gat ttg caa         528
Met His Gly Asp Thr Pro Thr Leu His Glu Tyr Met Leu Asp Leu Gln
                165                 170                 175 cca gag aca act gat ctc tac tgt tat gag caa tta aat gac agc tca         576
Pro Glu Thr Thr Asp Leu Tyr Cys Tyr Glu Gln Leu Asn Asp Ser Ser
                180                 185                 190 gag gag gag gat gaa ata gat ggt cca gct gga caa gca gaa ccg gac         624
Glu Glu Glu Asp Glu Ile Asp Gly Pro Ala Gly Gln Ala Glu Pro Asp
            195                 200                 205 aga gcc cat tac aat att gta acc ttt tgt tgc aag tgt gac tct acg         672
Arg Ala His Tyr Asn Ile Val Thr Phe Cys Cys Lys Cys Asp Ser Thr
        210                 215                 220 ctt cgg ttg tgc gta caa agc aca cac gta gac att cgt act ttg gaa         720
Leu Arg Leu Cys Val Gln Ser Thr His Val Asp Ile Arg Thr Leu Glu
225                 230                 235                 240 gac ctg tta atg ggc aca cta gga att gtg tgc ccc atc tgt tct cag         768
Asp Leu Leu Met Gly Thr Leu Gly Ile Val Cys Pro Ile Cys Ser Gln
                245                 250                 255 aaa cca aga tct cat cac cat cac cat cac taa                             801
Lys Pro Arg Ser His His His His His His
                260                 265

<210> SEQ ID NO 10
<211> LENGTH: 266
<212> TYPE: PRT
<213> ORGANISM: Artificial Sequence
<220> FEATURE:
<223> OTHER INFORMATION: Description of Artificial Sequence: Gene Fusion

<400> SEQUENCE: 10

Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
        50                  55                  60

Asn Pro Tyr Ala Val Cys Asp Lys Cys Leu Lys Phe Tyr Ser Lys Ile
 65                  70                  75                  80
```

```
Ser Glu Tyr Arg His Tyr Cys Tyr Ser Leu Tyr Gly Thr Thr Leu Glu
             85                  90                  95

Gln Gln Tyr Asn Lys Pro Leu Cys Asp Leu Leu Ile Arg Cys Ile Asn
        100                 105                 110

Cys Gln Lys Pro Leu Cys Pro Glu Glu Lys Gln Arg His Leu Asp Lys
    115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu Pro Gly
145                 150                 155                 160

Met His Gly Asp Thr Pro Thr Leu His Glu Tyr Met Leu Asp Leu Gln
                165                 170                 175

Pro Glu Thr Thr Asp Leu Tyr Cys Tyr Glu Gln Leu Asn Asp Ser Ser
            180                 185                 190

Glu Glu Glu Asp Glu Ile Asp Gly Pro Ala Gly Gln Ala Glu Pro Asp
        195                 200                 205

Arg Ala His Tyr Asn Ile Val Thr Phe Cys Cys Lys Cys Asp Ser Thr
    210                 215                 220

Leu Arg Leu Cys Val Gln Ser Thr His Val Asp Ile Arg Thr Leu Glu
225                 230                 235                 240

Asp Leu Leu Met Gly Thr Leu Gly Ile Val Cys Pro Ile Cys Ser Gln
                245                 250                 255

Lys Pro Arg Ser His His His His His His
                260                 265

<210> SEQ ID NO 11
<211> LENGTH: 519
<212> TYPE: DNA
<213> ORGANISM: Artificial Sequence
<220> FEATURE:
<221> NAME/KEY: CDS
<222> LOCATION: (1)..(516)
<220> FEATURE:
<223> OTHER INFORMATION: Description of Artificial Sequence: Gene Fusion

<400> SEQUENCE: 11 atg ggg aat cca tat gct gta tgt gat aaa tgt tta aag ttt tat tct      48
Met Gly Asn Pro Tyr Ala Val Cys Asp Lys Cys Leu Lys Phe Tyr Ser
  1               5                  10                  15 aaa att agt gag tat aga cat tat tgt tat agt ttg tat gga aca aca      96
Lys Ile Ser Glu Tyr Arg His Tyr Cys Tyr Ser Leu Tyr Gly Thr Thr
             20                  25                  30 tta gaa cag caa tac aac aaa ccg ttg tgt gat ttg tta att agg tgt     144
Leu Glu Gln Gln Tyr Asn Lys Pro Leu Cys Asp Leu Leu Ile Arg Cys
         35                  40                  45 att aac tgt caa aag cca ctg tgt cct gaa gaa aag caa aga cat ctg     192
Ile Asn Cys Gln Lys Pro Leu Cys Pro Glu Glu Lys Gln Arg His Leu
     50                  55                  60 gac aaa aag caa aga ttc cat aat ata agg ggt cgg tgg acc ggt cga     240
Asp Lys Lys Gln Arg Phe His Asn Ile Arg Gly Arg Trp Thr Gly Arg
 65                  70                  75                  80 tgt atg tct tgt tgc aga tca tca aga aca cgt aga gaa acc cag ctg     288
Cys Met Ser Cys Cys Arg Ser Ser Arg Thr Arg Arg Glu Thr Gln Leu
                 85                  90                  95 ccc ggg atg cat gga gat aca cct aca ttg cat gaa tat atg tta gat     336
Pro Gly Met His Gly Asp Thr Pro Thr Leu His Glu Tyr Met Leu Asp
            100                 105                 110 ttg caa cca gag aca act gat ctc tac tgt tat gag caa tta aat gac     384
Leu Gln Pro Glu Thr Thr Asp Leu Tyr Cys Tyr Glu Gln Leu Asn Asp
        115                 120                 125
```

```
agc tca gag gag gag gat gaa ata gat ggt cca gct gga caa gca gaa      432
Ser Ser Glu Glu Glu Asp Glu Ile Asp Gly Pro Ala Gly Gln Ala Glu
        130                 135                 140 ccg gac aga gcc cat tac aat att gta acc ttt tgt tgc aag tgt gac      480
Pro Asp Arg Ala His Tyr Asn Ile Val Thr Phe Cys Cys Lys Cys Asp
145                 150                 155                 160 tct acg ctt cgg aga tct cat cac cat cac cat cac taa                  519
Ser Thr Leu Arg Arg Ser His His His His His His
                165                 170
```

```
<210> SEQ ID NO 12
<211> LENGTH: 172
<212> TYPE: PRT
<213> ORGANISM: Artificial Sequence
<220> FEATURE:
<223> OTHER INFORMATION: Description of Artificial Sequence: Gene Fusion

<400> SEQUENCE: 12

Met Gly Asn Pro Tyr Ala Val Cys Asp Lys Cys Leu Lys Phe Tyr Ser
 1               5                  10                  15

Lys Ile Ser Glu Tyr Arg His Tyr Cys Tyr Ser Leu Tyr Gly Thr Thr
                20                  25                  30

Leu Glu Gln Gln Tyr Asn Lys Pro Leu Cys Asp Leu Leu Ile Arg Cys
            35                  40                  45

Ile Asn Cys Gln Lys Pro Leu Cys Pro Glu Glu Lys Gln Arg His Leu
        50                  55                  60

Asp Lys Lys Gln Arg Phe His Asn Ile Arg Gly Arg Trp Thr Gly Arg
 65                 70                  75                  80

Cys Met Ser Cys Cys Arg Ser Ser Arg Thr Arg Arg Glu Thr Gln Leu
                85                  90                  95

Pro Gly Met His Gly Asp Thr Pro Thr Leu His Glu Tyr Met Leu Asp
            100                 105                 110

Leu Gln Pro Glu Thr Thr Asp Leu Tyr Cys Tyr Glu Gln Leu Asn Asp
        115                 120                 125

Ser Ser Glu Glu Glu Asp Glu Ile Asp Gly Pro Ala Gly Gln Ala Glu
    130                 135                 140

Pro Asp Arg Ala His Tyr Asn Ile Val Thr Phe Cys Cys Lys Cys Asp
145                 150                 155                 160

Ser Thr Leu Arg Arg Ser His His His His His His
                165                 170
```

```
<210> SEQ ID NO 13
<211> LENGTH: 519
<212> TYPE: DNA
<213> ORGANISM: Artificial Sequence
<220> FEATURE:
<221> NAME/KEY: CDS
<222> LOCATION: (1)..(519)
<220> FEATURE:
<223> OTHER INFORMATION: Description of Artificial Sequence: Gene Fusion

<400> SEQUENCE: 13 atg gag gag gat gaa ata gat ggt cca gct gga caa gca gaa ccg gac       48
Met Glu Glu Asp Glu Ile Asp Gly Pro Ala Gly Gln Ala Glu Pro Asp
 1               5                  10                  15 aga gcc cat tac aat att gta acc ttt tgt tgc aag tgt gac tct acg       96
Arg Ala His Tyr Asn Ile Val Thr Phe Cys Cys Lys Cys Asp Ser Thr
                20                  25                  30 ctt cgg ttg tgc gta caa agc aca cac gta gac att cgt act ttg gaa      144
Leu Arg Leu Cys Val Gln Ser Thr His Val Asp Ile Arg Thr Leu Glu
            35                  40                  45
```

-continued

```
gac ctg tta atg ggc aca cta gga att gtg tgc ccc atc tgt tct cag      192
Asp Leu Leu Met Gly Thr Leu Gly Ile Val Cys Pro Ile Cys Ser Gln
     50                  55                  60 aaa cca gga tct cat atg cac caa aag aga act gca atg ttt cag gac      240
Lys Pro Gly Ser His Met His Gln Lys Arg Thr Ala Met Phe Gln Asp
 65                  70                  75                  80 cca cag gag cga ccc aga aag tta cca cag tta tgc aca gag ctg caa      288
Pro Gln Glu Arg Pro Arg Lys Leu Pro Gln Leu Cys Thr Glu Leu Gln
                 85                  90                  95 aca act ata cat gat ata ata tta gaa tgt gtg tac tgc aag caa cag      336
Thr Thr Ile His Asp Ile Ile Leu Glu Cys Val Tyr Cys Lys Gln Gln
            100                 105                 110 tta ctg cga cgt gag gta tat gac ttt gct ttt cgg gat tta tgc ata      384
Leu Leu Arg Arg Glu Val Tyr Asp Phe Ala Phe Arg Asp Leu Cys Ile
        115                 120                 125 gta tat aga gat ggg aat cca tat gct gta tgt gat aaa tgt tta aag      432
Val Tyr Arg Asp Gly Asn Pro Tyr Ala Val Cys Asp Lys Cys Leu Lys
130                 135                 140 ttt tat tct aaa att agt gag tat aga cat tat tgt tat agt ttg tat      480
Phe Tyr Ser Lys Ile Ser Glu Tyr Arg His Tyr Cys Tyr Ser Leu Tyr
145                 150                 155                 160 gga aca aca tta aga tct cat cac cat cac cat cac taa                  519
Gly Thr Thr Leu Arg Ser His His His His His His
                165                 170
```

<210> SEQ ID NO 14
<211> LENGTH: 172
<212> TYPE: PRT
<213> ORGANISM: Artificial Sequence
<220> FEATURE:
<223> OTHER INFORMATION: Description of Artificial Sequence: Gene Fusion

<400> SEQUENCE: 14

```
Met Glu Glu Asp Glu Ile Asp Gly Pro Ala Gly Gln Ala Glu Pro Asp
 1               5                  10                  15

Arg Ala His Tyr Asn Ile Val Thr Phe Cys Cys Lys Cys Asp Ser Thr
                20                  25                  30

Leu Arg Leu Cys Val Gln Ser Thr His Val Asp Ile Arg Thr Leu Glu
            35                  40                  45

Asp Leu Leu Met Gly Thr Leu Gly Ile Val Cys Pro Ile Cys Ser Gln
        50                  55                  60

Lys Pro Gly Ser His Met His Gln Lys Arg Thr Ala Met Phe Gln Asp
 65                  70                  75                  80

Pro Gln Glu Arg Pro Arg Lys Leu Pro Gln Leu Cys Thr Glu Leu Gln
                 85                  90                  95

Thr Thr Ile His Asp Ile Ile Leu Glu Cys Val Tyr Cys Lys Gln Gln
            100                 105                 110

Leu Leu Arg Arg Glu Val Tyr Asp Phe Ala Phe Arg Asp Leu Cys Ile
        115                 120                 125

Val Tyr Arg Asp Gly Asn Pro Tyr Ala Val Cys Asp Lys Cys Leu Lys
130                 135                 140

Phe Tyr Ser Lys Ile Ser Glu Tyr Arg His Tyr Cys Tyr Ser Leu Tyr
145                 150                 155                 160

Gly Thr Thr Leu Arg Ser His His His His His His
                165                 170
```

<210> SEQ ID NO 15
<211> LENGTH: 12
<212> TYPE: DNA

```
<213> ORGANISM: Artificial Sequence
<220> FEATURE:
<223> OTHER INFORMATION: Description of Artificial Sequence: Primer

<400> SEQUENCE: 15
tgctctagag ca                                                              12
```

VARIANTS OF HUMAN PAPILLOMAVIRUS ANTIGENS

FIELD OF THE INVENTION

This invention relates generally to variants of human papilloma virus (HPV) antigens, and in particular it relates to non-transforming variants of HPV antigens which are suitable for use in vaccines. The invention also extends to vaccine compositions which include these variants of HPV antigens as active immunogens, as well as to methods of use of these variants to elicit an immune response against HPV.

BACKGROUND OF THE INVENTION

Papillomaviruses are small DNA viruses that infect a variety of animal species. Some are associated with the development of malignancies in their natural hosts. Over 60 types of human papillomavirus (HPV) have been identified. These infect humans at a variety of body locations and are responsible for common skin warts, laryngeal papillomas, genital warts and other wart-like lesions. Genital HPV infections are particularly common and a number of HPV types, but most frequently types 6, 11, 16 and 18, infect the genital tract in both men and women. In women, HPVs infect various portions of the genital tract including the cervix.

Genital HPVs are a significant clinical problem. HPV infection of the ano-genital region is now regarded as the most common form of viral sexually-transmitted disease (STD). The viruses cause genital infections which become manifest in one of three ways:

i clinical infection, where gross genital warts are visible;
 ii subclinical infection, where viral lesions are not obvious but are detectable using special viewing techniques; and
 iii latency, where the only sign of infection is the presence of HPV DNA.

Subclinical infections are common. It is estimated that 2 to 4% of Papanicolaou (Pap.) smears show evidence of HPV. Latent infections are even more frequent and the majority of adults harbour one or more types of genital HPV.

Carcinoma of the uterine cervix (CaCx) is a common cancer in women. Two forms of cervical cancer are recognised; squamous cell carcinoma (SCC) is by far the most frequent representing about 90% of observed cases; adenocarcinoma, a cancer of the secretion cells, accounts for about 10%. Cancer of the cervix develops through pre-cancerous intermediate stages to invasive forms (the carcinoma) which can become life threatening. The pre-cancerous stages of increasing severity are known as cervical intraepithelial neoplasia (CIN) grades 1 to 3. Over a 20 year period about 40% of the untreated CIN3 patients develop invasive cancer, the increasingly serious forms of which are known as stage I to IV. Invasive cancer frequently leads to death.

Cervical cancer in both its pre-cancerous and invasive stages is one of the few cancers for which a highly reliable and relatively cheap screening method is available. The Papanicolaou (Pap.) smear involves cytological examination of cervical scrapes to test for the presence of abnormal cervical cells which are indicative of pre- or invasive cancer. Detection of abnormalities leads to further investigation and treatment if necessary.

To be effective at reducing the number of cervical cancers and resultant deaths, Pap. smear screening is undertaken on a mass scale and ideally includes all women of sexually-active age. Detection and subsequent treatment of CIN has a very high success rate in the prevention of invasive cancer, while early detection of the latter can have a marked effect on mortality.

Most developed countries have highly developed Pap. smear screening programs which have resulted in a 30% drop in age-specific mortality due to CaCx between 1960 and 1980. However, apart from the Scandinavian countries, few developed countries screen more than 50 to 60% of women, allowing CaCx and resultant deaths to remain a significant problem. In the developing world the situation is even worse as few organised screening programs exist, resulting in 400,000 new cases of invasive cancer annually in these countries.

As outlined earlier, a variety of types of HPV cause genital infections in humans, although four types (6, 11, 16, 18) predominate. Evidence collected over the past 15 years strongly suggests that several of the HPVs are associated with the development of cervical cancer. Indeed many researchers have concluded that specific HPV types are the essential aetiologic factor responsible for the development of many of the cancers.

Infection with HPV-16 and HPV-18 has been associated with the development of cancer of the cervix. It has been postulated that HPV acts as an initiator in cervical carcinogenesis and that malignant transformation depends on interaction with other factors. Infections with HPV-6 and HPV-11 have been associated with the development of genital warts. The incidence of HPV infection appears to be increasing as shown by a large increase recently in patient visits related to genital HPV infections in both males and females and the presence of HPV in Pap. smears of some women under 30 years of age.

The nature of HPV-16 in particular and papilloma viruses in general has been well studied recently. HPV-16 contains a 7904 bp double-stranded DNA genome (Siedorf, K. et al., *Virology* (1985) 145:181–185). The capsid is 50 nm and contains 72 capsomers (Klug, A., *J. Mol. Biol.* (1965) 11:403–423). U.S. Pat. No. 4,777,239 discloses a series of 17 synthetic peptides which are said to be capable of raising antibodies to HPV-16 and thus may be useful for diagnostic purposes. In addition, European Patent 0 412 762 discloses polypeptides which are antagonists of the biochemical interaction of the HPV E7 protein and the retinoblastoma gene (RBG) protein, and which are said to be useful in the treatment of genital warts and cervical cancer.

The DNAs of several papilloma viruses have been sequenced, including several HPV types, bovine papillomavirus (BPV) and cottontail rabbit papillomavirus (CRPV). All of these display similar patterns of nucleotide sequence with respect to open reading frames. The open reading frames can be functionally divided into early regions (E) and late regions (L); the E regions are postulated to encode proteins needed for replication and transformation; and the L regions to encode the viral capsid proteins (Danos, O., et al., *J. Invest. Derm.* (1984) 83:7s–11s).

Two HPV encoded proteins, E6 and E7, are thought to be involved in the pathogenesis of HPV-induced abnormal cell proliferation (reviewed in Stoppler et al., *Intervirology*, (1994) 37:168–179). The amino acid sequences of the HPV-16 E6 and E7 proteins as deduced from the nucleic acid sequence are shown in Siedorf et al., *Virology*, (1985) 145:181–185.

The HPV genes encoding the E6 and E7 proteins are invariably expressed in tissue or tumor cells obtained from cervical cancers associated with HPV infection. In addition, the HPV E6 and E7 genes derived from the HPV-16 strain are capable of inducing epithelial cell transformation in cell culture without the presence of other HPV genes. These observations indicate that at least part of the stimulation of cell proliferation caused by HPV infection is due to the E6 and E7 viral proteins.

The HPV E6 and E7 proteins are believed to be effective immunological targets for tumour regression. As described above, however, the E6 and E7 genes are known to "transform" cells possibly by the action of their protein products in interfering with cellular proteins involved in the control cell growth. Accordingly, if even minute traces of DNA encoding the E6 and E7 proteins were to be present in a vaccine preparation, this could cause that vaccine preparation to initiate irreversible transformation events in the cells of a recipient of the vaccine preparation. It is an object of the present invention to provide non-transforming variants of the HPV E6 and E7 proteins which are able to induce in a host animal (particularly a human) a range of humoral and cellular immune responses, and which are therefore suitable for use in the production of vaccines for the prevention, prophylaxis, therapy and treatment of HPV-induced diseases or other conditions which would benefit from inhibition of HPV infection.

In the work leading to the present invention, it has been recognised that there are four ways to induce immune responses to E6 and/or E7 proteins:
  (i) use whole proteins (this introduces the possibility that contaminating DNA may be associated with the proteins);
  (ii) use point mutants (this can lead to reversion to native protein, which requires multiple mutations to avoid; in addition, any point mutation leads to loss of potentially vital epitopes);
  (iii) use specific peptides (this requires a very large number of peptides, the identification of which is very complex, to make a vaccine of broad utility); and
  (iv) use variants such as fusions and combinations of deletion mutants (this method has none of the above limitations).

In addition to the cell transforming properties of the E7 protein itself, fusions of this protein with β-galactosidase have also been shown to be cell-transforming (Fujikawa et al., *Virology*, 204, 789–793, 1994). Accordingly, it could not be predicted that fusions of E6 and/or E7 moieties, either full length or non-full length, would not also be cell-transforming.

SUMMARY OF THE INVENTION

In one aspect the present invention provides as an isolated protein, a variant of the HPV E6 or E7 protein which variant is able to elicit a humoral and/or cellular immune response against HPV in a host animal but which is not cell-transforming in the host animal.

In another aspect, the present invention provides a method for eliciting an immune response against HPV in a host animal, which method comprises administering to the host animal an effective amount of a variant of the HPV E6 or E7 protein which variant is able to elicit a humoral and/or cellular immune response against HPV in a host animal but which is not cell-transforming in the host animal.

In yet another aspect, the present invention provides a vaccine composition for use in eliciting an immune response against HPV in a host animal, which comprises a variant of the HPV E6 or E7 protein which variant is able to elicit a humoral and/or immune response against HPV in a host animal but which is not cell-transforming in the host animal, and optionally an adjuvant, together with a pharmaceutically acceptable carrier and/or diluent.

The invention also extends to the use of a variant of the HPV E6 or E7 protein which variant is able to elicit a humoral and/or cellular immune response against HPV in a host animal but which is not cell-transforming in the host animal, and optionally an adjuvant, in eliciting an immune response against HPV in a host animal.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

Figure 1A:
FIGS. 1(a)–(d) show domain maps for the different proteins referenced herein.

As used herein, references to the variant of this invention as being "not cell-transforming in the host animal" mean that the cell-transforming property of the "parent" or wild-type HPV E6 or E7 protein has been reduced, and preferably effectively eliminated, in the variant. In particular, these references indicate that this cell-transforming property has been significantly reduced in comparison with wild-type E6 or E7 protein in appropriate test systems.

It will be appreciated that where the non-transforming variant HPV E6 or E7 protein of this invention is produced by expression of an appropriate encoding recombinant DNA molecule, the nature of that encoding DNA, unlike the wild-type E6 or E7 genes, would not have the potential to initiate irreversible transformation events in the cells of the host animal.

The variant HPV E6 or E7 proteins of the present invention include, but are not limited to, deletion mutants of the wild-type E6 or E7 proteins in the form of non-full length fragments of the wild-type proteins, as well as fusion proteins in which E6 and/or E7 moieties are fused, optionally with a linkage of from 1 to 50, preferably a short linkage of from 1 to 20, and more preferably from 1 to 5, amino acid residues between the E6 and/or E7 moieties. The E6 and/or E7 moieties in such a fusion protein may comprise the full wild-type E6 or E7 proteins, or alternatively they may comprise non-full length fragments of the wild-type proteins. The fusion proteins may also comprise other moieties fused or otherwise coupled thereto, for example moieties to assist in purification of the fusion protein (for example, a glutathione-S-transferase or GST moiety or hexa-His moiety) or to enhance the immunogenicity of the fusion protein (for example an adjuvant such as diphtheria or cholera toxin or a non-toxic derivative thereof such as the holotoxoid or B sub-unit of cholera toxin).

The term "non-full length fragment" is used herein to describe polypeptides which may for example comprise deletion mutants of the E6 or E7 proteins corresponding to at least 50%, more preferably 60–70%, and even 80–90% of the full-length E6 or E7 protein sequence. By way of example only, the fragments may be deletion mutants corresponding to the N-terminal or C-terminal two-thirds of the E6 or E7 proteins.

Suitable non-full length fragments, and fusion proteins which comprise the E6 and/or E7 proteins or non-full length fragments thereof, as described above may be readily produced by techniques which are well known in the art and which are described by way of example below. It will be appreciated by persons skilled in this art that variant HPV E6 or E7 proteins as described above including fusion proteins which comprise various combinations of the E6 and/or E7 moieties may be readily produced using these. known techniques, and then tested using routine methods to establish whether the resultant fusion protein or other variant protein meets the criteria of the present invention, that is whether it is able to elicit a humoral and/or cellular immune response in a host animal but is not cell-transforming in the host animal.

Preferably, the host animal is a human, however the host animal may also be a non-human mammal.

The present invention is particularly, but not exclusively, directed to variants of the E6 or E7 proteins of the HPV-16 and HPV-18 genotypes, however it will be appreciated that the invention extends to variants of the corresponding proteins in other HPV genotypes, particularly the HPV-6 and HPV-11 genotypes which are causative agents of condylomata acuminta, and other genotypes which have oncogenic potential of a type similar to HPV-16 and HPV-18.

Previous work in this area has shown that vaccination of rats with live viral vectors expressing HPV E6 or E7 proteins leads to rejection of transplanted E7-bearing tumour cells (Meneguzzi et al., *Virology*, 181:62–69, 1991), while vaccination of cattle with an adjuvanted HPV E7 vaccine leads to accelerated rejection of tumours induced by bovine papillomavirus (Campo, *Cancer Cells*, 3:421–426, 1991).

The variant HPV E6 or E7 proteins of the present invention are provided as isolated proteins, that is they are substantially free of other HPV proteins, and find particular utility for the treatment of genital warts, cervical cancer or other conditions caused by HPV in man. The variant proteins can be included in pharmaceutical compositions for the treatment or prevention of diseases involving HPV as well as the other conditions discussed above.

The variant HPV E6 or E7 proteins of the invention may be used to raise antibodies andlor induce cellular immune responses, either in subjects for which protection against infection by HPV is desired, i.e. as prophylactic vaccines, or to heighten the immune response to an HPV infection already present, i.e. as therapeutic vaccines. They also can be injected into production species to obtain antisera. In lieu of the polyclonal antisera obtained in the production species, monoclonal antibodies may be produced using the standard methods or by more recent modifications thereof by immortalising spleen or other antibody-producing cells for injection into animals to obtain antibody-producing clones. The polyclonal or monoclonal antibodies obtained, corrected if necessary for species variations, can also be used as therapeutic agents.

Direct administration of the variant proteins to a host can confer either protective immunity against HPV or, if the subject is already infected, a boost to the subject's own immune response to more effectively combat the progress of the HPV induced disease.

The magnitude of the prophylactic or therapeutic dose of a variant HPV E6 or E7 protein of this invention will, of course, vary with the group of patients (age, sex, etc.), the nature or the severity of the condition to be treated and with the particular variant protein and its route of administration. In general, the weekly dose range for use lies within the range of from about 0.1 to about 5 $\mu$g per kg body weight of a mammal.

Any suitable route of administration may be employed for providing a mammal, especially a human, with an effective dosage of a variant protein of this invention. For example, oral, rectal, vaginal, topical, parenteral, ocular, nasal, sublingual, buccal, intravenous and the like may be employed. Dosage forms include tablets, troches, dispersions, suspensions, solutions, capsules, creams, ointments, suppositories, aerosols and the like. Said dosage forms also include injected or implanted slow releasing devices specifically designed for this purpose or other forms of implants modified to additionally act in this fashion.

If the variant proteins are to be administered as vaccines, they are formulated according to conventional methods for such administration to the subject to be protected. If the antibodies are to be used for therapeutic purposes, it is generally desirable to confer species characteristics upon them compatible with the subject to be treated. Accordingly, it is often desirable to prepare these antibodies in monoclonal form since fusion with suitable partners is capable of conferring the desired characteristics on the secreted monoclonals.

The variant proteins may be delivered in accordance with this invention in ISCOMS™ (immune stimulating complexes), liposomes or encapsulated in compounds such as acrylates or poly(DL-lactide-co-glycoside) to form microspheres. The variant proteins may also be incorporated into oily emulsions and delivered orally.

Other adjuvants, as well as conventional pharmaceutically acceptable carriers, excipients, buffers or diluents, may also be included in the vaccine compositions of this invention. Generally, a vaccine composition in accordance with the present invention will comprise an immunologically effective amount of the variant HPV E6 or E7 protein, and optionally an adjuvant, in conjunction with one or more conventional pharmaceutically acceptable carriers and/or diluents. An extensive though not exhaustive list of adjuvants can be found in Coulter and Cox, "Advances in Adjuvant Technology and Application", in *Animal Parasite Control Utilizing Biotechnology*, Chapter 4, Ed. Young, W. K., CRC Press, 1992. As used herein "pharmaceutically acceptable carriers and/or diluents" include any and all solvents, dispersion media, aqueous solutions, coatings, antibacterial and antifungal agents, isotonic and absorption delaying agents and the like. The use of such media and agents for pharmaceutical active substances is well known in the art and is described by way of example in *Remington's Pharmaceutical Sciences*, 18th Edition, Mack Publishing Company, Pennsylvania, U.S.A.

In practical use, a variant protein of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous and intra-arterial). In preparing the compositions for oral dosage form, any of the usual pharmaceutical media may be employed, such as, for example, water glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar-coated or enteric-coated by standard techniques.

In addition to the common dosage forms set out above, the variant proteins of this invention may also be administered by controlled release means and/or delivery devices, including by way of example, the controlled release preparations disclosed in International Patent Specification No. PCT/AU93/00677 (Publication No. WO 94/15636).

Pharmaceutical compositions of the present invention suitable for oral or parenteral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or fmely divided solid carriers or both, and then, if necessary, shaping the product into the desired presentation.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

Cloning and Expression of GST E6/E7 Fusion Protein

A molecule consisting of HPV-16 E6 and E7 sequences as an "in-frame" fusion was created as follows. A clone of HPV-16 DNA containing both E6 and E7 genomic sequences served as the template for separate PCR amplification of E6 and E7 using oligonucleotides:

(a) (5')CGCTCGAGAGATCTCATATGCACC-AAAAGAGAACTGC(3') and (b) (5')CGCCCGGGCAGCTGGGTTTCTCTACGTG(3') for E6; and (c) (5')CGCCCGGGATGCATGGAGATACA-CCTACATTGCATG(3') and (d) (5')CGGTCGACGGATCCTGGTTTCT-GAGAACAGATGGG(3') for E7.

A SmaI recognition site at the 3' end of Et and the 5' end of E7 facilitated the fusion and introduced two additional amino acids (proline and glycine) between E6 and E7. Additional restriction enzyme recognition sites at the 5' and 3' boundaries of the fusion molecule (introduced in the oligonucleotides) aided in subsequent cloning procedures.

Figure 2:
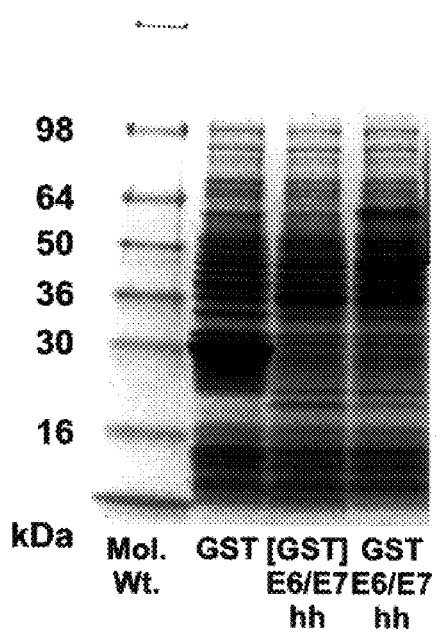
FIG. 2 shows amounts of fusion protein produced in transformed cells following IPTG induction in Example 1.
Figure 3:
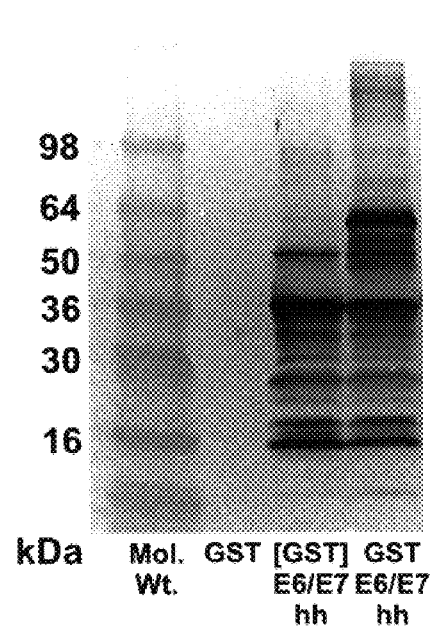
FIG. 3 shows a western blot of a protein described in Example 2.

The fused E6/E7 sequence was cloned as a BglII-BamH1 fragment into vector pDS56 (Stuber et al., *EMBO J.*, (1984) 3:3143–3148) which provided an in-frame 3' hexa-his(hh) sequence. From this, E6/E7hh was removed as a EcoRI/Hind III fragment and subdloned into pGEM 7+3, which was created by inserting the BamH1/HindIII portion of the pGEM3-Zf(+)(Promega) polylinker into the BamH1/HindIII site of the multiple cloning site of the pGEM7-Zf (+)(Promega) vector. E6/E7hh was then removed from pGEM7+3 as a EcoRI/Sal I fragment and inserted into the multiple cloning site of pGEX-4T-1 (Pharmacia) to produce pGEX-4T-1 E6/E7hh. This plasmid was used to transform a variety of *E. coli* strains including TOPP2 (Stratagene) and BL21 (Amrad/Pharmacia). Both types of transformed cells produced a significant amount of fuision protein following IPTG induction (FIG. 2). The fusion protein (GST E6/E7hh represented schematically in FIG. 1a) was in the expected size range of around 60 kDa. The identity of the protein was confirmed by Western blots probed with two monoclonal antibodies directed against E7 (LHIL.16E7.8F and LHIL.16E7.6D, Tindle et al. *Journal of General Virology*, (1990) 71:1347–1354) (FIG. 3).

EXAMPLE 2

Cloning and Expression of E6/E7 Fusion Protein

Figure 1B:

In order to express E6/E7 hh as protein lacking GST, a termination codon was introduced into pGEX-4T-1 E6/E7hh at a unique BalI site 3' to, and in-frame with, the GST translation initiation codon using the phosphorylated linker TGCTCTAGAGCA. After transforming *E. coli* strain BL21 with this new plasmid ([GST] E6/E7hh) a significant amount of protein (E6/E7hh, represented schematically in FIG. 1b) was produced following IPTG induction at a size of approximately 33 kD which corresponds to the size expected of a E6/E7hh fusion protein (FIG. 2). Identity of this protein was confirmed by Western blot using the same monoclonal antibodies as in Example 1 (FIG. 3).

EXAMPLE 3

Cloning and Expression of Deleted (Non-full Length) Forms of E6 and E7

(i) Construction of ΔE6C/ΔE7N

Full length E6/E7 in pGEM3(Promega) served as a template for PCR amplification of deleted forms of E6/E7 using oligonucleotides 5'GCGCGAATTCTATTAAGGAGC-CCGGGATGGGGAATCCATATGCTGTAT3' and 5'CGC-GAGATCTCCGAAGCGTAGAGTCACACTTG3'.

Figure 1C:
Figure 4A:
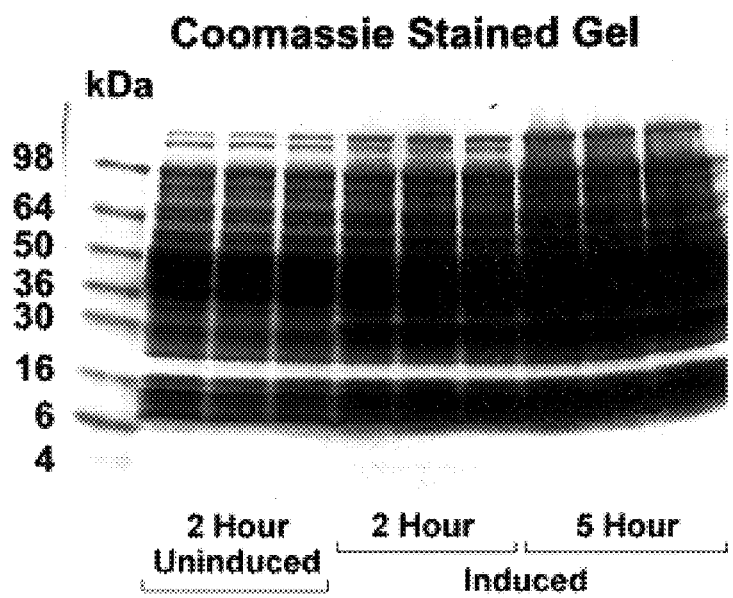
FIG. 4(a) shows a coomassie stained gel indicating amounts of fusion protein produced in transformed cells following IPTG induction in Example 3(i).
Figure 4B:
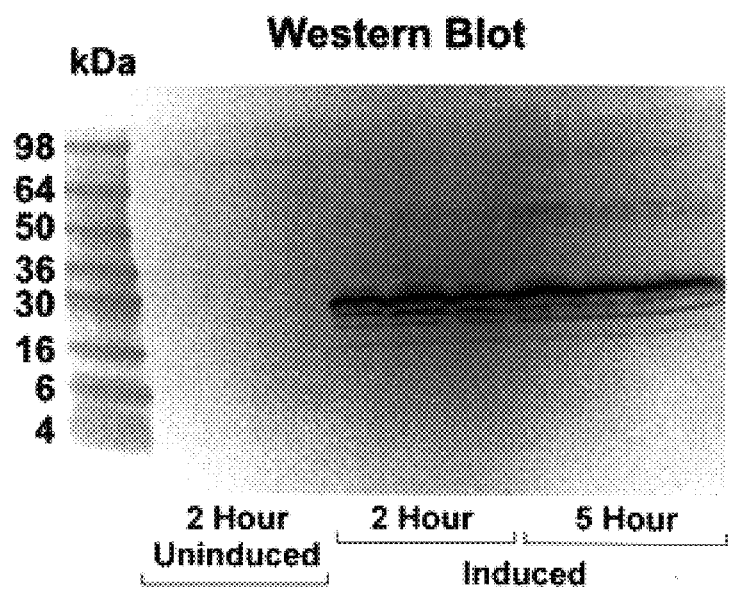
FIG. 4(b) is a western blot confirming the identity of the protein of Example 3(i).

The resulting truncation of E6/E7 lacking sequences (189 bp) at the N terminal of E6 and C terminal of E7 (96 bp) was subcloned into pGEX-4T-1 containing a termination codon in the GST sequence to produce [GST] ΔE6C/ΔE7Nhh. This plasmid was used to transform *E. coil* strain BL21. Transformed cells expressed a significant amount of fusion protein (ΔE6C/ΔE7Nhh, represented schematically in FIG. 1c) following IPTG induction (FIG. 4a) producing a protein of the approximate expected size (20 kD). The identity of this protein was confirmed by Western blot using the same monoclonal antibodies as in Example 1 (FIG. 4b).

(ii) Construction of ΔE7C/ΔE6N

Figure 1D:
Figure 5A:
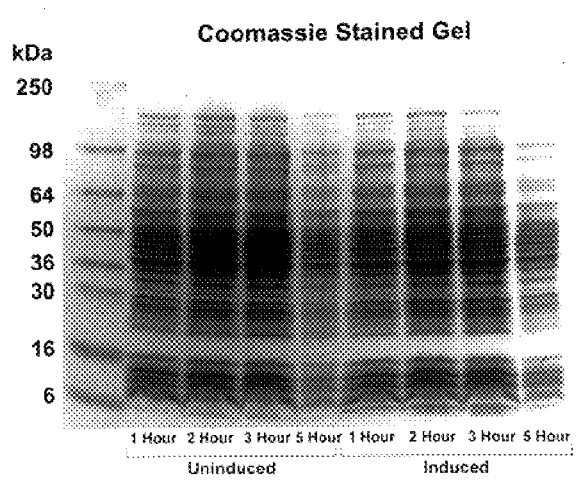
FIG. 5(a) shows a coomassie stained gel indicating amounts of fusion protein produced in transformed cells following IPTG induction in Example 3(ii).
Figure 5B:
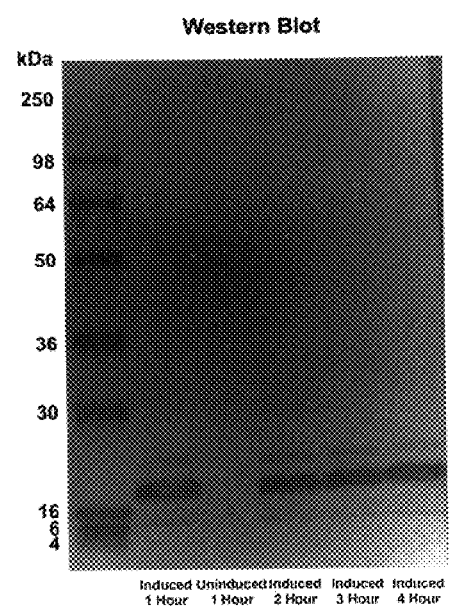
FIG. 5(b) is a western blot confirming the identity of the protein of Example 3(ii).

Using oligonucleotides (a) in Example 1 and 5'CGC-CCGGGTAATGTTGTTCCATACAAACTA3' an N-terminal representation of E6 comprising 285 bp was amplified from the same HPV-16 clone utilised in Example 1. As well, oligonucleotides 5'CGCCCGGGGAGGAG-GAGGATGAAATAGATG3' and (d) in Example 1 were used to produce a 198 bp C-terminal E7 sequence. These were each blunt cloned into pGEM7-Zf(+) (Promega). A fusion cassette was formed by restricting the E6 clone with KpnI/BglII and inserting the E7 sequence upstream as a KpnI/BamHI fragment. This fused sequence was then reamplified with SmaI and BglII cloning sites for insertion into pGEX-4T-1 containing a termination codon in the GST sequence to produce [GST] ΔE7C/ΔE6Nhh. After transformation into *E. coli* BL21, protein production was assayed by PAGE followed by Coomassie staining and Western blotting (FIGS. 5*a* and 5*b*). A protein (ΔE7C/ΔE6Nhh, represented schematically in FIG. 1*d*) of the expected size (20 kD) was evident on Western blots.

EXAMPLE 4

DNA Sequencing of E6/E7 Full Length and Deletion Constructs

E6/E7 constructs were sequenced in both directions by the dideoxy method using primers that generated overlapping sequence information. The $^{T7}$ Sequencing™ Kit (Pharmacia) was used to generate $^{35}$S-labelled chain-terminated fragments which were analysed on a Sequi-Gen™ (Biorad) electrophoretic gel apparatus. The DNA and corresponding amino acid sequences for E6/E7hh (PPV162.DNA), ΔE6C/ΔE7Nhh (CAD600.SEQ) and ΔE7C/ΔE6Nhh (C620.TXT) are set out below.

```
5' ATG CAC CAA AAG AGA ACT GCA ATG TTT CAG GAC CCA CAG GAG CGA CCC AGA AAG
    --- --- --- --- --- --- --- --- --- --- --- --- --- --- --- --- ---
    Met His Gln Lys Arg Thr Ala Met Phe Gln Asp Pro Gln Glu Arg Pro Arg Lys

TTA CCA CAG TTA TGC ACA GAG CTG CAA ACA ACT ATA CAT GAT ATA ATA TTA GAA
    --- --- --- --- --- --- --- --- --- --- --- --- --- --- --- --- ---
    Leu Pro Gln Leu Cys Thr Glu Leu Gln Thr Thr Ile His Asp Ile Ile Leu Glu

TGT GTG TAC TGC AAG CAA CAG TTA CTG CGA CGT GAG GTA TAT GAC TTT GCT TTT
    --- --- --- --- --- --- --- --- --- --- --- --- --- --- --- --- ---
    Cys Val Tyr Cys Lys Gln Gln Leu Leu Arg Arg Glu Val Tyr Asp Phe Ala Phe

CGG GAT TTA TGC ATA GTA TAT AGA GAT GGG AAT CCA TAT GCT GTA TGT GAT AAA
    --- --- --- --- --- --- --- --- --- --- --- --- --- --- --- --- ---
    Arg Asp Leu Cys Ile Val Tyr Arg Asp Gly Asn Pro Tyr Ala Val Cys Asp Lys

TGT TTA AAG TTT TAT TCT AAA ATT AGT GAG TAT AGA CAT TAT TGT TAT AGT TTG
    --- --- --- --- --- --- --- --- --- --- --- --- --- --- --- --- ---
    Cys Leu Lys Phe Tyr Ser Lys Ile Ser Glu Tyr Arg His Tyr Cys Tyr Ser Leu

TAT GGA ACA ACA TTA GAA CAG CAA TAC AAC AAA CCG TTG TGT GAT TTG TTA ATT
    --- --- --- --- --- --- --- --- --- --- --- --- --- --- --- --- ---
    Tyr Gly Thr Thr Leu Glu Gln Gln Tyr Asn Lys Pro Leu Cys Asp Leu Leu Ile

AGG TGT ATT AAC TGT CAA AAG CCA CTG TGT CCT GAA GAA AAG CAA AGA CAT CTG
    --- --- --- --- --- --- --- --- --- --- --- --- --- --- --- --- ---
    Arg Cys Ile Asn Cys Gln Lys Pro Leu Cys Pro Glu Glu Lys Gln Arg His Leu

CAG AAA AAG CAA AGA TTC CAT AAT ATA AGG GGT CGG TGG ACC GGT CGA TGT ATG
    --- --- --- --- --- --- --- --- --- --- --- --- --- --- --- --- ---
    Asp Lys Lys Gln Arg Phe His Asn Ile Arg Gly Arg Trp Thr Gly Arg Cys Met

TCT TGT TGC AGA TCA TCA AGA ACA CGT AGA GAA ACC CAG CTG CCC GGG ATG CAT
    --- --- --- --- --- --- --- --- --- --- --- --- --- --- --- --- ---
    Ser Cys Cys Arg Ser Ser Arg Thr Arg Arg Glu Thr Gln Leu Pro Gly Met His

GGA GAT ACA CCT ACA TTG CAT GAA TAT ATG TTA GAT TTG CAA CCA GAG ACA ACT
    --- --- --- --- --- --- --- --- --- --- --- --- --- --- --- --- ---
    Gly Asp Thr Pro Thr Leu His Glu Tyr Met Leu Asp Leu Gln Pro Glu Thr Thr

GAT CTC TAC TGT TAT GAG CAA TTA AAT GAC AGC TCA GAG GAG GAG GAT GAA ATA
    --- --- --- --- --- --- --- --- --- --- --- --- --- --- --- --- ---
    Asp Leu Tyr Cys Tyr Glu Gln Leu Asn Asp Ser Ser Glu Glu Glu Asp Glu Ile

GAT GGT CCA GCT GGA CAA GCA GAA CCG GAC AGA GCC CAT TAC AAT ATT GTA ACC
    --- --- --- --- --- --- --- --- --- --- --- --- --- --- --- --- ---
    Asp Gly Pro Ala Gly Gln Ala Glu Pro Asp Arg Ala His Tyr Asn Ile Val Thr

TTT TGT TGC AAG TGT GAC TCT ACG CTT CGG TTG TGC GTA CAA AGC ACA CAC GTA
    --- --- --- --- --- --- --- --- --- --- --- --- --- --- --- --- ---
    Phe Cys Cys Lys Cys Asp Ser Thr Leu Arg Leu Cys Val Gln Ser Thr His Val

GAC ATT CGT ACT TTG GAA GAC CTG TTA ATG GGC ACA CTA GGA ATT GTG TGC CCC
    --- --- --- --- --- --- --- --- --- --- --- --- --- --- --- --- ---
    Asp Ile Arg Thr Leu Glu Asp Leu Leu Met Gly Thr Leu Gly Ile Val Cys Pro

ATC TGT TCT CAG AAA CCA AGA TCT CAT CAC CAT CAC CAT CAC TAA 3'
    --- --- --- --- --- --- --- --- --- --- --- --- --- ---
    Ile Cys Ser Gln Lys Pro Arg Ser His His His His His His ***
```

File: CAD600.SEQ
Range: 1- 519 Mode: Normal
Codon: Universal

```
                                                                54
5' ATG GGG AAT CCA TAT GCT GTA TGT GAT AAA TGT TTA AAG TTT TAT TCT AAA ATT
   --- --- --- --- --- --- --- --- --- --- --- --- --- --- --- --- --- ---
   Met Gly Asn Pro Tyr Ala Val Cys Asp Lys Cys Leu Lys Phe Tyr Ser Lys Ile

AGT GAG TAT AGA CAT TAT TGT TAT AGT TTG TAT GGA ACA ACA TTA GAA CAG CAA
   --- --- --- --- --- --- --- --- --- --- --- --- --- --- --- --- --- ---
   Ser Glu Tyr Arg His Tyr Cys Tyr Ser Leu Tyr Gly Thr Thr Leu Glu Gln Gln

TAC AAC AAA CCG TTG TGT GAT TTG TTA ATT AGG TGT ATT AAC TGT CAA AAG CCA
   --- --- --- --- --- --- --- --- --- --- --- --- --- --- --- --- --- ---
   Ile Asn Cys Gln Lys Pro Tyr Asn Lys Pro Leu Cys Asp Leu Leu Ile Arg Cys

CTG TGT CCT GAA GAA AAG CAA AGA CAT CTG GAC AAA AAG CAA AGA TTC CAT AAT
   --- --- --- --- --- --- --- --- --- --- --- --- --- --- --- --- --- ---
   Leu Cys Pro Glu Glu Lys Gln Arg His Leu Asp Lys Lys Gln Arg Phe His Asn

ATA AGG GGT CGG TGG ACC GGT CGA TGT ATG TCT TGT TGC AGA TCA TCA AGA ACA
   --- --- --- --- --- --- --- --- --- --- --- --- --- --- --- --- --- ---
   Ile Arg Gly Arg Trp Thr Gly Arg Cys Met Ser Cys Cys Arg Ser Ser Arg Thr

CGT AGA GAA ACC CAG CTG CCC GGG ATG CAT GGA GAT ACA CCT ACA TTG CAT GAA
   --- --- --- --- --- --- --- --- --- --- --- --- --- --- --- --- --- ---
   Arg Arg Glu Thr Gln Leu Pro Gly Met His Gly Asp Thr Pro Thr Leu His Glu

TAT ATG TTA GAT TTG CAA CCA GAG ACA ACT GAT CTC TAC TGT TAT GAG CAA TTA
   --- --- --- --- --- --- --- --- --- --- --- --- --- --- --- --- --- ---
   Tyr Met Leu Asp Leu Gln Pro Glu Thr Thr Asp Leu Tyr Cys Tyr Glu Gln Leu

AAT GAC AGC TCA GAG GAG GAG GAT GAA ATA GAT GGT CCA GCT GGA CAA GCA GAA
   --- --- --- --- --- --- --- --- --- --- --- --- --- --- --- --- --- ---
   Asn Asp Ser Ser Glu Glu Glu Asp Glu Ile Asp Gly Pro Ala Gly Gln Ala Glu

CCG GAC AGA GCC CAT TAC AAT ATT GTA ACC TTT TGT TGC AAG TGT GAC TCT ACG
   --- --- --- --- --- --- --- --- --- --- --- --- --- --- --- --- --- ---
   Pro Asp Arg Ala His Tyr Asn Ile Val Thr Phe Cys Cys Lys Cys Asp Ser Thr

CTT CGG AGA TCT CAT CAC CAT CAC CAT CAC TAA 3'
   --- --- --- --- --- --- --- --- --- --- ---
   Leu Arg Arg Ser His His His His His His ***
```

File: C620.TXT
Range: 1- 519 Mode: Normal
Codon Table: Universal

```
5' ATG GAG GAG GAT GAA ATA GAT GGT CCA GCT GGA CAA GCA GAA CCG GAC AGA GGC
   --- --- --- --- --- --- --- --- --- --- --- --- --- --- --- --- --- ---
   Met Glu Glu Asp Glu Ile Asp Gly Pro Ala Gly Gln Ala Glu Pro Asp Arg Ala

CAT TAC AAT ATT GTA ACC TTT TGT TGC AAG TGT GAC TCT ACG CTT CGG TTG TGC
   --- --- --- --- --- --- --- --- --- --- --- --- --- --- --- --- --- ---
   His Tyr Asn Ile Val Thr Phe Cys Cys Lys Cys Asp Ser Thr Leu Arg Leu Cys

GTA CAA AGC ACA CAC GTA GAC ATT CGT ACT TTG GAA GAC CTG TTA ATG GGC ACA
   --- --- --- --- --- --- --- --- --- --- --- --- --- --- --- --- --- ---
   Val Gln Ser Thr His Val Asp Ile Arg Thr Leu Glu Asp Leu Leu Met Gly Thr

CTA GGA ATT GTG TGC CCC ATC TGT TCT CAG AAA CCA GGA TCT CAT ATG CAC CAA
   --- --- --- --- --- --- --- --- --- --- --- --- --- --- --- --- --- ---
   Leu Gly Ile Val Cys Pro Ile Cys Ser Gln Lys Pro Gly Ser His Met His Gln

AAG AGA ACT GCA ATG TTT CAG GAC CCA CAG GAG CGA CCC AGA AAG TTA CCA CAG
   --- --- --- --- --- --- --- --- --- --- --- --- --- --- --- --- --- ---
   Lys Arg Thr Ala Met Phe Gln Asp Pro Gln Glu Arg Pro Arg Lys Leu Pro Gln

TTA TGC ACA GAG CTG CAA ACA ACT ATA CAT GAT ATA ATA TTA GAA TGT GTG TAC
   --- --- --- --- --- --- --- --- --- --- --- --- --- --- --- --- --- ---
   Leu Cys Thr Glu Leu Gln Thr Thr Ile His Asp Ile Ile Leu Glu Cys Val Tyr

TGC AAG CAA CAG TTA CTG CGA CGT GAG GTA TAT GAC TTT GCT TTT CGG GAT TTA
   --- --- --- --- --- --- --- --- --- --- --- --- --- --- --- --- --- ---
   Cys Lys Gln Gln Leu Leu Arg Arg Glu Val Tyr Asp Phe Ala Phe Arg Asp Leu

TGC ATA GTA TAT AGA GAT GGG AAT CCA TAT GCT GTA TGT GAT AAA TGT TTA AAG
   --- --- --- --- --- --- --- --- --- --- --- --- --- --- --- --- --- ---
   Cys Ile Val Tyr Arg Asp Gly Asn Pro Tyr Ala Val Cys Asp Lys Cys Leu Lys
```

-continued

```
TTT TAT TCT AAA ATT AGT GAG TAT AGA CAT TAT TGT TAT AGT TTG ATA GGA ACA
--- --- --- --- --- --- --- --- --- --- --- --- --- --- --- --- --- ---
Phe Tyr Ser Lys Ile Ser Glu Tyr Arg His Tyr Cys Tyr Ser Leu Tyr Gly Thr

ACA TTA AGA TCT CAT CAC CAT CAC CAT CAC TAA 3'
--- --- --- --- --- --- --- --- --- --- ---
Thr Leu Arg Ser His His His His His His ***
```

EXAMPLE 5

Immunogenicity of E6/E7hh Protein

A. Purification of E6/E7hh

Figure 6A:
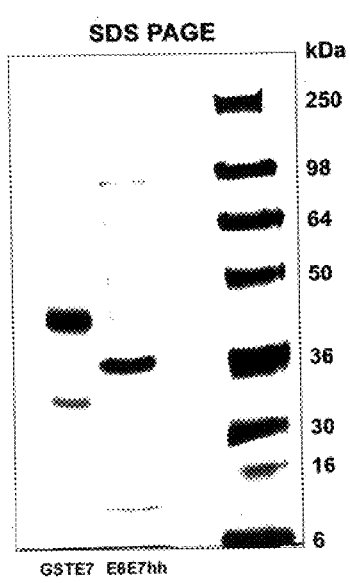
FIGS. 6(a) and (b) show coomassie stained gel and western blot, respectively, confirming purity and identity of the product of Example 5.
Figure 6B:
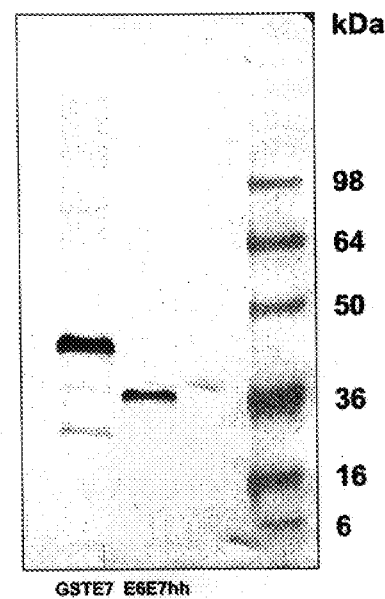

E. coli cells (strain BL21) containing the [GST] E6/E7hh plasmid were induced using 0.1–0.5 mM IPTG and harvested 3–4 hours after induction. The cells were pelleted by low speed centrifugation and inclusion bodies containing the E6/E7hh protein isolated by sonication and centrifugation. The inclusion pellet was solubilised in 7M Urea or 6M Guanidine HCl and subjected to nickel chelate column chromatography (Porath et.al., *Biochemistry* 22, 1621–1630, 1983). Protein was eluted using either an increasing gradient of imidazole or a decreasing pH gradient, and fractions containing E6/E7hh pooled and dialysed against 25 mM Tris, 0.5M NaCl, 1% NOG, 10 mM DTT pH7.5. The identity and purity of the dialysed product was determined by Coomassie stained polyacrylamide gel electrophoresis and Western blot using the monoclonal antibodies referred to in Example 1 (FIGS. 6a and 6b).

B. Immunogenicity of E6/E7hh

On day 0, two groups of 5 C57BL/6 mice (8 weeks old, female) were inoculated subcutaneously at the base of the tail with 0.1 mL of a formulation containing 6 μg ISCOMATRIX™, 19 μg E6/E7hh (purified as in A. above) in PBS pH7.2. A second dose of the formulation was administered at day 14 to group 1, and at day 17 to group 2. At day 21 and 24, mice in groups 1 and 2 (respectively) were bled. Serum antibody responses to E6/E7hh were then measured using the following solid phase EIA:

Nunc MaxiSorp EIA plates were coated with E6/E7hh by incubating 0.1 mL/well for 2 hours at 37° of a 10 μg/mL solution in 4M urea in 50 mM carbonate buffer, pH 9.5. The liquid was removed, and the plates were further incubated at 37° for 1 hour with 0.2 mL/well of 1 mg/mL casein in PBS pH 7.2. After 6 washes, 0.1 mL/well of test serum (diluted in PBS pH 7.2, 1 mg/mL casein, 0.5% Tween 20, 0.002% alphazurine A) was added, and the plates incubated for 1 hour at 37°. The plates were then again washed 6× with PBS pH 7.2, 0.5% Tween 20. To detect bound antibody, 0.1 mL of 0.1 μg/ml KPL horseradish peroxidase-labelled goat anti-mouse IgG+IgM (H and L chain specific) in PBS pH 7.2, 1 mg/mL casein, 0.5% Tween 20, 0.002% alphazurine A was added to each well. The plates were incubated for 1 hour at 20°, washed 6× with PBS pH 7.2, 0.5% v/v Tween 20, then 0.1 mL of enzyme substrate (3,3',5,5'tetramethylbenzidine/$H_2O_2$ formulation, purchased from KPL) was then added. After 10 minutes incubation at 20°, the reaction was stopped by addition of 50 μl of 0.5M $H_2SO_4$. The coloured product was then measured at 450 nm in a vertical beam spectrophotometer. Titres were expressed as the reciprocal of the serum dilution resulting in an optical density value of 0.1.

Table 1 shows that all mice of both groups 1 and 2 produced a significant response following immunization. Titres ranged from 3.17 to 5.66 (expressed in the $\log_{10}$ of the reciprocal dilution resulting in the optical density of 0.1 in the solid phase EIA described above). Pre-existing antibody levels were low or undetectable (measured in sera obtained on day 0 immediately prior to inoculation).

Clearly, the E6/E7hh fusion protein is highly immunogenic when administered to mice by this procedure.

As well, E6/E7hh was found to produce specific delayed-type hypersensitivity (DTH) following one dose of a formulation containing E6/E7hh plus ISCOM™ adjuvant. The mice produced specific DTH responses to both E6 and E7 when challenged in the ear with small doses of purified GST-E6 or GST-E7 proteins.

TABLE 1

| | Log dilution to 0.1 OD. | | | | | | | | | |
|---|---|---|---|---|---|---|---|---|---|---|
| Group/mouse | 1/1 | 1/2 | 1/3 | 1/4 | 1/5 | 2/1 | 2/2 | 2/3 | 2/4 | 2/5 |
| pre-bleed | <2 | <2 | <2 | <2 | <2 | <2 | 2.06 | <2 | <2 | <2 |
| final bleed | 3.66 | 5.66 | 3.23 | 3.19 | 3.79 | 4.19 | 4.21 | 3.71 | 5.55 | 3.17 |

EXAMPLE 6

Transformation Studies of E6/E7 Gene Construct

An E6/E7 fusion DNA construct was subcloned into the multiple cloning site of plasmid vector pJ4Ω (Wilkinson et al., *J. Exp. Med.* (1988) 167:1442–58) as a BamHI fragment to produce pJ4Ω E6/E7. For comparison purposes pJ4Ω vectors containing HPV16 E6 (pJ4Ω E6) and HPV16 E7 (pJ4ΩE7) ORFs were used. Where neomycin selection was required, the pcDNA3 vector (Invitrogen) containing a neomycin resistance marker was utilised. These plasmids were amplified in *E. coli* and plasmid DNA extracted by alkaline lysis and purified on resin (Qiagen) eluted, ethanol precipitated and resuspended in $H_2O$. DNA quantity and purity was determined by spectrophotometric measurement at 260 and 280 nm. DNA integrity was checked by electrophoresis in 1% agarose gels and ethidium bromide staining. Target cells for transformation were mouse NIH 3T3 cells (CSL Biosciences). The cells were routinely propagated on Minimal Essential Medium (Eagle) supplemented with non-essential amino acids, 2 mM glutamine and 10% foetal bovine serum (growth medium).

Transfection of NIH 3T3 cells with plasmid DNA was carried out essentially as described in the Promega Technical Bulletin No. 216 using Tfx™-50 to enhance DNA uptake. Typical transfection mixtures contained 5 μg of test plasmid (pJ4ΩE6/E7, pJ4ΩE7 or pJ4ΩE6 and pJ4ΩE7), and where required 0.1 μg pcDNA3. Where pJ4ΩE6 and pJ4ΩE7 were cotransfected 2.5 μg of each was used.

Cells were grown to approximately 80% confluency, the growth medium removed and plasmid DNA mixed with Tfx™-50 in a ratio of 4:1 in Minimal Essential Medium was added and the cells incubated at 37° C.

Following 1–2 hours incubation at 37° C. the transfection mixture was removed and fresh growth medium added. After 48 hours incubation at 37° C. transfected cells were removed by trysinization and either assayed for colony formation in soft agar or incubated for a further 24 hours at 37° C. before neomycin selection was applied.

For assay of colony formation in soft agar the trysinized cells were resuspended at a density of $1-5 \times 10^5$ cells/mL in RPMI 1640 supplemented with 10% FBS, 2 mM glutamine, 10 mM Hepes and 0.084% $NaHCO_3$ (RPMI1640+) and containing 0.4% agarose (Seaplaque low gelling temperature, FMC Bioproducts, USA) maintained at a temperature of 37° C. Following mixing 2.5 mL of this suspension was added to each well of a 6 well tray (Nunc) and allowed to set. The trays were then incubated for a period of 10–14 days at 37° C. in an atmosphere of 5% $CO_2$, prior to counting of colonies using an inverted light microscope.

Selection of neomycin resistant colonies was carried out on subconfluent cell monolayers using RPMI 1640+ containing 700 µg/mL neomycin (Geneticin). The monolayers were incubated at 37° C. in an atmosphere of 5% $CO_2$ for 10–14 days prior to counting of neomycin resistant colonies using an inverted light microscope. Following counting, the colonies were dispersed by trysinization and assayed for colony formation in soft agar as described above. The results of a neomycin selection experiment following transfection of 3T3 cells with various plasmid constructs are presented in Table 2.

TABLE 2

| Construct (+pcDNA3) | No. of neomycin resistant colonies | Mean no. of cells per colony |
|---|---|---|
| pJ4ΩE6/E7 | 2 | 10 |
| pJ4ΩE7 | 4 | >65 |
| pJ4ΩE6 + pJ4ΩE7 | 11 | >66 |

These results indicate that the E6/E7 fusion is only weakly transforming in comparison with E7 or E6+E7. Both colony numbers and cell growth for the E6/E7 fusion were low in comparison with the unfused wild-type sequences. This indicates that the outcome of fusing the E6 and E7 sequences is impairment of the ability of these sequences to promote cell transformation.

Persons skilled in this art will appreciate that variations and modifications may be made to the invention as broadly described herein, other than those specifically described without departing from the spirit and scope of the invention. It is to be understood that this invention extends to include all such variations and modifications.

We claim:

1. An isolated variant human papillomavirus (HPV) protein able to elicit an immune response against HPV in a host animal but not being cell-transforming in said host animal, wherein said variant protein comprises a fusion protein comprising a HPV E6 protein selected from the group consisting of full length E6 protein and non-full length deletion mutants thereof, and a HPV E7 protein selected from the group consisting of full length E7 protein and non-full length deletion mutants thereof, and optionally a linker linking said E6 and E7 proteins.

2. An isolated variant HPV protein according to claim 1, wherein said protein further comprises a foreign protein or peptide fused or otherwise coupled to one or both of said E6 and E7 proteins.

3. An isolated variant HPV protein according to claim 2, wherein the foreign protein or peptide is selected from the group consisting of (i) proteins or peptides to assist in purification of the fusion protein or (ii) proteins or peptides to enhance the immunogenicity of the fusion protein.

4. An isolated variant HPV protein acording to claim 1, which comprises a fusion protein comprising a full length E6 protein fused to a full length E7 protein.

5. An isolated variant HPV protein according to claim 4, which comprises the full length E6 protein as an N-terminal sequence of the fusion protein and the full length E7 protein as a C-terminal sequence of the fusion protein.

6. An isolated variant HPV protein according to claim 4, which comprises the full length E7 protein as an N-terminal sequence of the fusion protein and the full length E6 protein as a C-terminal sequence of the fusion protein.

7. An isolated variant HPV protein according to claim 1, which is a fusion protein comprising a non-full length deletion mutant of the E6 protein as an N-terminal sequence of the fusion protein and a non-full length deletion mutant of the E7 protein as a C-terminal sequence of the fusion protein.

8. An isolated variant HPV protein according to claim 1, which is a fusion protein comprising a non-full length deletion mutant of the E7 protein as an N-terminal sequence of the fusion protein and a non-full length deletion mutant of the E6 protein as a C-terminal sequence of the fusion protein.

9. An isolated variant HPV protein according to claim 1, wherein the non-full length deletion mutants of the E6 or E7 proteins comprise at least 50% of the full length sequences of the proteins.

10. An isolated variant HPV protein according to claim 9, wherein the non-full length deletion mutants of the E6 or E7 protein comprise at least 60% of the full-length sequences of the proteins.

11. An isolated variant HPV protein according to claim 10, wherein the non-full length deletion mutants of the E6 or E7 proteins comprise at least the N-terminal 60% of the full length sequence of the proteins.

12. An isolated variant HPV protein according to claim 10, wherein the non-full length deletion mutants of the E6 or E7 proteins comprise at least the C-terminal 60% of the full length sequence of the proteins.

13. An isolated variant HPV protein according to claim 1, wherein said linker consists of from 1 to 50 amino acid residues.

14. An isolated variant HPV protein according to claim 13, wherein said linker consists of from 1 to 20 amino acid residues.

15. An isolated variant HPV protein according to claim 4, wherein said linker consists of from 1 to 5 amino acid residues.

16. An isolated variant HPV protein according to claim 1, wherein said E6 or E7 protein is selected from the group consisting of HPV-16, HPV-18, HPV-6 and HPV-11 genotypes.

17. An isolated variant HPV protein according to claim 16, wherein said E6 or E7 protein is selected from the group consisting of HPV-16 and HPV-18 genotypes.

18. A composition for use in eliciting an immune response against HPV in a host animal, said composition comprising an isolated variant HPV protein acording to claim 1, together with a pharmaceutically acceptable carrier and/or diluent.

19. A composition according to claim 18, further comprising an adjuvant.

20. A method for eliciting an immune response against HPV in a host animal, which method comprises administering to the host animal an effective amount of an isolated variant HPV protein according to claim 1.

21. A method according to claim 20, wherein said variant HPV protein is administered in a composition together with a pharmaceutically acceptable carrier and/or diluent.

22. A method according to claim 21, wherein said composition further comprises an adjuvant.

23. A method according to claim 20, wherein said host animal is a human.

* * * * *